United States Patent [19]

Guerriero

[11] Patent Number: 4,619,261

[45] Date of Patent: Oct. 28, 1986

[54] HYDROSTATIC PRESSURE DEVICE FOR BLEEDING CONTROL THROUGH AN INFLATABLE, STITCHABLE AND RETRIEVABLE BALLOON-NET SYSTEM

[76] Inventor: Frederico Guerriero, 1212 N. Lake Shore Dr., Chicago, Ill. 60610

[21] Appl. No.: 639,381

[22] Filed: Aug. 9, 1984

[51] Int. Cl.⁴ .............................................. A61B 17/12
[52] U.S. Cl. ................................ 128/325; 128/334 R; 128/344; 604/97
[58] Field of Search ................... 128/325, 334 R, 344, 128/DIG. 25; 604/97

[56] References Cited

U.S. PATENT DOCUMENTS

| | | | |
|---|---|---|---|
| 1,051,850 | 1/1913 | Sandmark | 128/325 |
| 3,171,410 | 3/1965 | Towle et al. | 128/325 |
| 3,766,924 | 10/1973 | Pidgeon | 128/325 |
| 3,874,387 | 4/1975 | Barbieri | 128/325 |
| 4,102,342 | 7/1978 | Akiyama et al. | 128/325 |
| 4,338,941 | 7/1982 | Payton | 128/344 |
| 4,428,375 | 1/1984 | Ellman | 128/325 |

FOREIGN PATENT DOCUMENTS 2460130  2/1981  France .............................. 128/325

OTHER PUBLICATIONS

"Instructions for Blood Vessel Occluders", 3-1968, VIVO.

Primary Examiner—Gene Mancene
Assistant Examiner—John G. Weiss
Attorney, Agent, or Firm—Alan R. Thiele

[57] ABSTRACT

A hydrostatic pressure application device for stopping bleeding from an internal wound has a balloon captured within the confines of a net. The net is secured to the area surrounding the wound by sutures tied in surgical thread so that when hydraulic pressure is applied by connecting flexible tubing to the balloon causing it to expand, the capturing of the balloon within the net will cause pressure to be applied to the surface of the wound, thus stopping any bleeding. The device and the surgical threads are removable through an incision when the bleeding from the internal wound has stopped.

10 Claims, 11 Drawing Figures

HYDROSTATIC PRESSURE DEVICE FOR BLEEDING CONTROL THROUGH AN INFLATABLE, STITCHABLE AND RETRIEVABLE BALLOON-NET SYSTEM

FIELD OF THE INVENTION

The present invention generally relates to devices for stopping bleeding by the application of direct pressure. More particularly, the device of the present invention is concerned with the stopping of bleeding from an internal wound by the direct application of hydraulic pressure at the site of the bleeding by a device which may be easily removed when the bleeding from the internal wound has stopped.

BACKGROUND OF THE INVENTION

During major surgery bleeding may occur at various internal wounds located within the body. Herein the term "wound" is used in its most generic sense. For example, an ulcerated and bleeding carcinoma of the stomach would be a wound, hemorrhaging varicose veins from the esophagus would also be a wound, bleeding from a paraspinal vessel would be considered a wound, also a weak and leaking vascular suture would be a wound. Bleeding from each one of these wounds is normally stopped by direct application of finger pressure by a member of the surgical team. During operative procedures, time may not permit stopping the operation or extending the duration of the operation until bleeding from the wound ceases. When the bleeding continues after the operative procedures are complete, the site of the wound may be packed with gauze until the bleeding stops.

The need, therefore, exists to provide a device which will apply prolonged direct pressure to a bleeding wound both during the time period that additional operative procedures are being carried out and after the period that the operative procedures have been completed. Additionally, pressure on the wound should be controllable from outside of the body of the patient. Even with today's advanced surgical practices, there are still clinical pathological situations which result in bleeding from the gastrointestinal tract where more blood is thrown out of the vascular system than can be replaced by transfusion of fresh blood through the veins. In that case, agressive surgery could become too risky. In this situation, a simple laparotomy with hydrostatic pressure control on the bleeding area could be life saving. In addition, the control of the vascular oozing could be prolonged for days until the conditions are more manageable.

In contrast with the gauze-packing pressure application method, the present invention provides a selective controllable, pressure application system using a hydrostatic column which, unlike the gauze packing method, is not influenced by the movements of the compressed organ. This is because the device of the present invention is stitched to the organ itself where the bleeding area circumscribed by the stitches is unchangeable.

Finally, in order to minimize the risk to the patient, the device for applying pressure to the point of internal bleeding should be easily removable from the body after the bleeding from the internal wound has stopped.

The use of hydraulic pressure devices to apply direct pressure to a wound for the control of bleeding was recognized in U.S. Pat. Nos. 1,051,850 to Sandmark and 2,179,964 to Stevens. These two patents illustrate devices which may be inserted in the nasal passage to stop nasal bleeding by the use of an inflatable device. The application of hydraulic or pneumatic pressure to the exterior surface of the body was recognized in U.S. Pat. Nos. 3,171,410 to Towle et al, 3,625,219 to Abrams, 3,874,387 to Barbieri, and 4,233,980 to McRae et al. None of the devices can be used for direct application of pressure to the site of internal bleeding.

While not related to the stoppage of bleeding, U.S. Pat. No. 4,207,891 to Bolduc, envisions the use of an inflatable device for the application of medication within the uterine cavity of a female. While describing the use of an inflatable device within the body of a patient, this device is not to be used for the problem of stopping bleeding from an internal wound by the application of direct pressure.

Consequently, a void exists in the art for a device which can be used to apply direct pressure to an internal bleeding wound during and after the completion of surgical procedures. Additionally, a need exists in the art to provide a device which can be easily removed from the body once bleeding from the internal wound has stopped.

SUMMARY OF THE INVENTION

A hydrostatic pressure application device consists of an expansible flexible container or balloon connected to a tube which conducts fluid into the balloon. A net or bag made from an open weave fabric surrounding the balloon, is used to position and secure the balloon over an internal wound so that when fluid is conducted into the balloon it will expand, thus applying direct pressure to the bleeding wound. The application of direct pressure by the balloon to the wound will stop blood flow. In particular, when used within the body of a patient the net is secured at several points to the area surrounding the internal wound by releasable sutures. Fluid from a fluid source is conducted by flexible tubing into the balloon within the net. This causes the hydraulic head pressure from the fluid source to be directed by the balloon to the surface of the wound. The net surrounding the balloon prevents the balloon from moving away from the wound when hydraulic pressure is applied to the balloon. The tubing which supplies hydraulic pressure to the balloon and the surgical thread attaching the net to the area surrounding the wound both pass through a small incision in the body of the patient so that when it is desired to release hydraulic pressure from the wound and remove the device, the knots securing the surgical thread are released and the entire device is withdrawn through an incision.

BRIEF DESCRIPTION OF THE DRAWINGS

A better understanding of the device of the present invention may be had by reference to the drawings wherein.

DESCRIPTION OF THE EMBODIMENT

Figure 1:
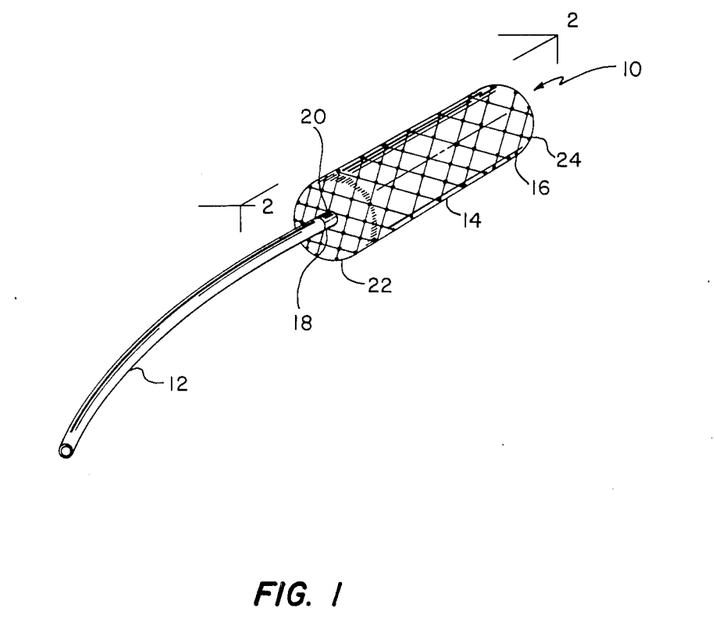
FIG. 1 is a perspective view of the hemostatic pressure device of this invention.
Figure 2:
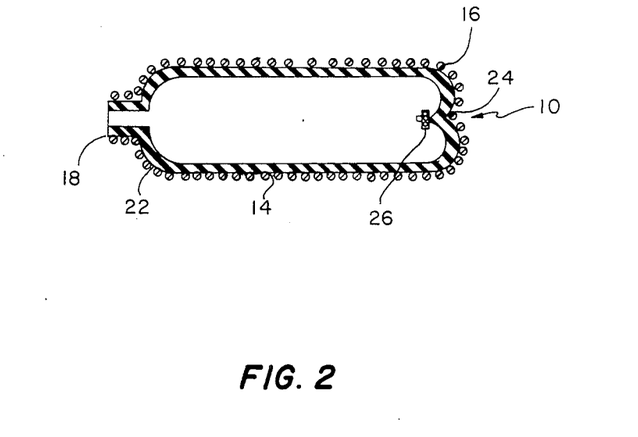
FIG. 2 is a sectional view taken at line 2—2 of FIG. 1.

As best seen in FIGS. 1 and 2, the hydrostatic pressure device of the present invention, generally 10 consists of three main parts: a tube 12, a flexible container or balloon 14 and a net 16. While net 16 may be only attached at point 18 where tube 12 enters balloon 14 by collar 20 as shown in FIG. 1, it has proven to be the better method to attach the net 16 not only at base 22 of balloon 14 but also at head 24 of balloon 14. This attachment to head 24 of balloon 14 is accomplished by turning balloon 14 inside out and inserting net 16 into balloon 14. In the preferred embodiment, a metal ferrule 26 is used to crimp net 16 and balloon 14 together. It will be understood that other attachment means such as a suitable cement may be used in place of ferrule 26. Balloon 14 is then turned back on itself so that net 16 is on the outside of balloon 14. Net 16 may then be secured to tube 12 by collar 20. While attachment of net 16 is accomplished by collar 20 in the preferred embodiment, it will be understood that any suitable attachment means such as a compatible cement may be employed. For illustrative purposes the thicknesses of the cross sections of balloon 14 and net 16 are shown greatly exaggerated in FIG. 2.

Figure 3:
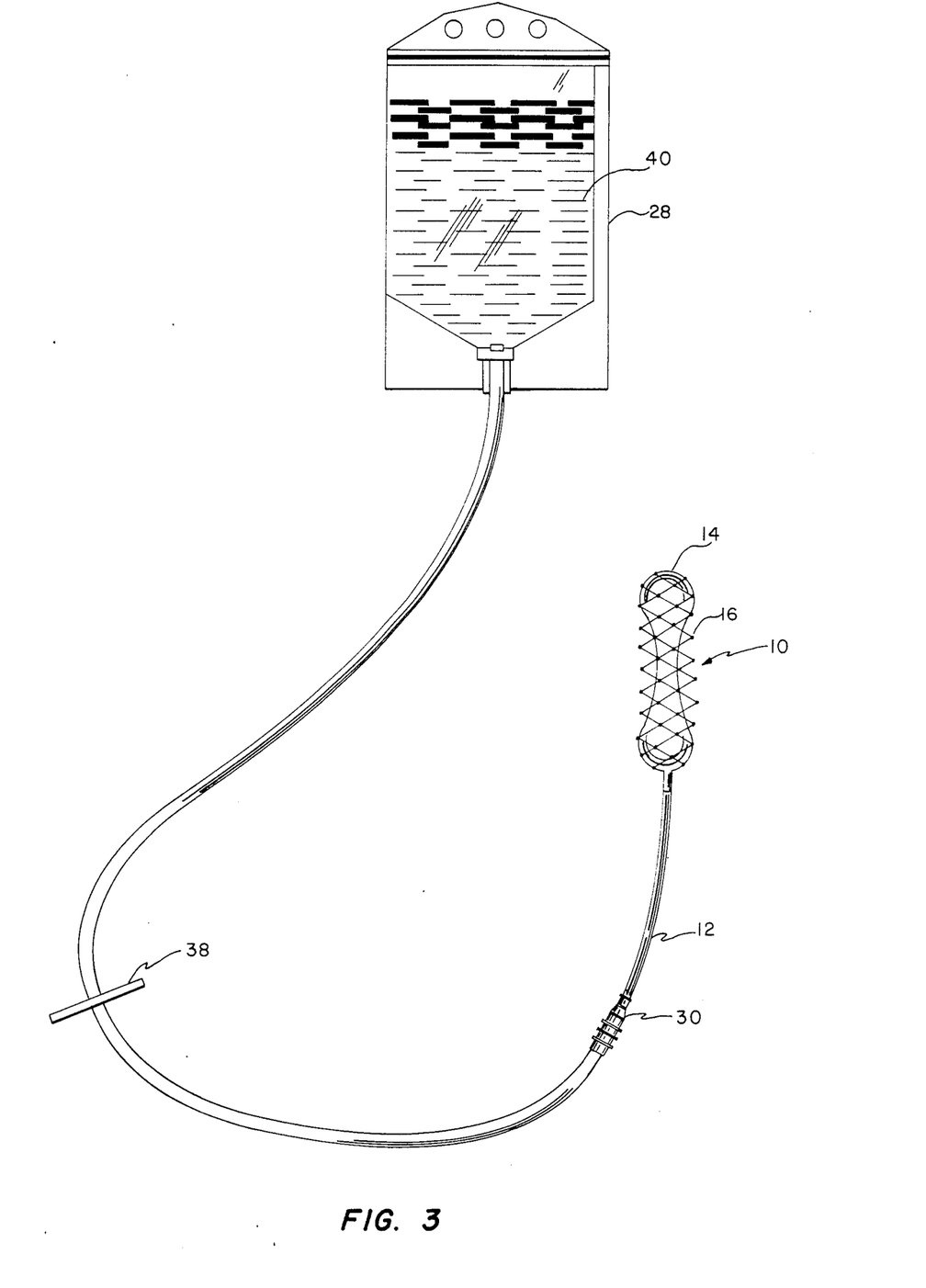
FIG. 3 is a front elevational view of the device of the present invention as part of a fluid pressure system before the application of hydraulic pressure.
Figure 4:
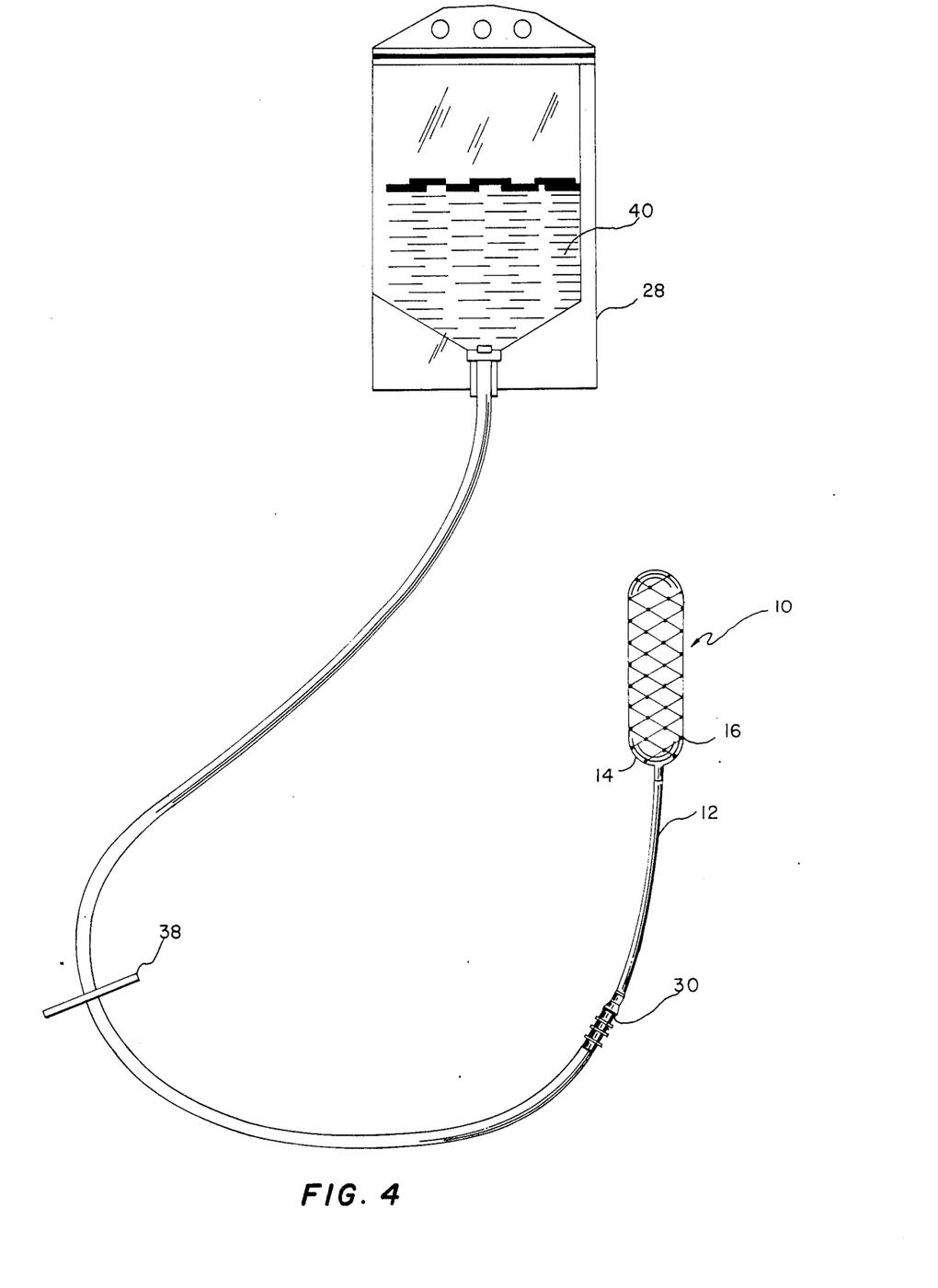
FIG. 4 is a front elevational view of the device of the present invention as part of a fluid pressure system after the application of fluid pressure.
Figure 5:
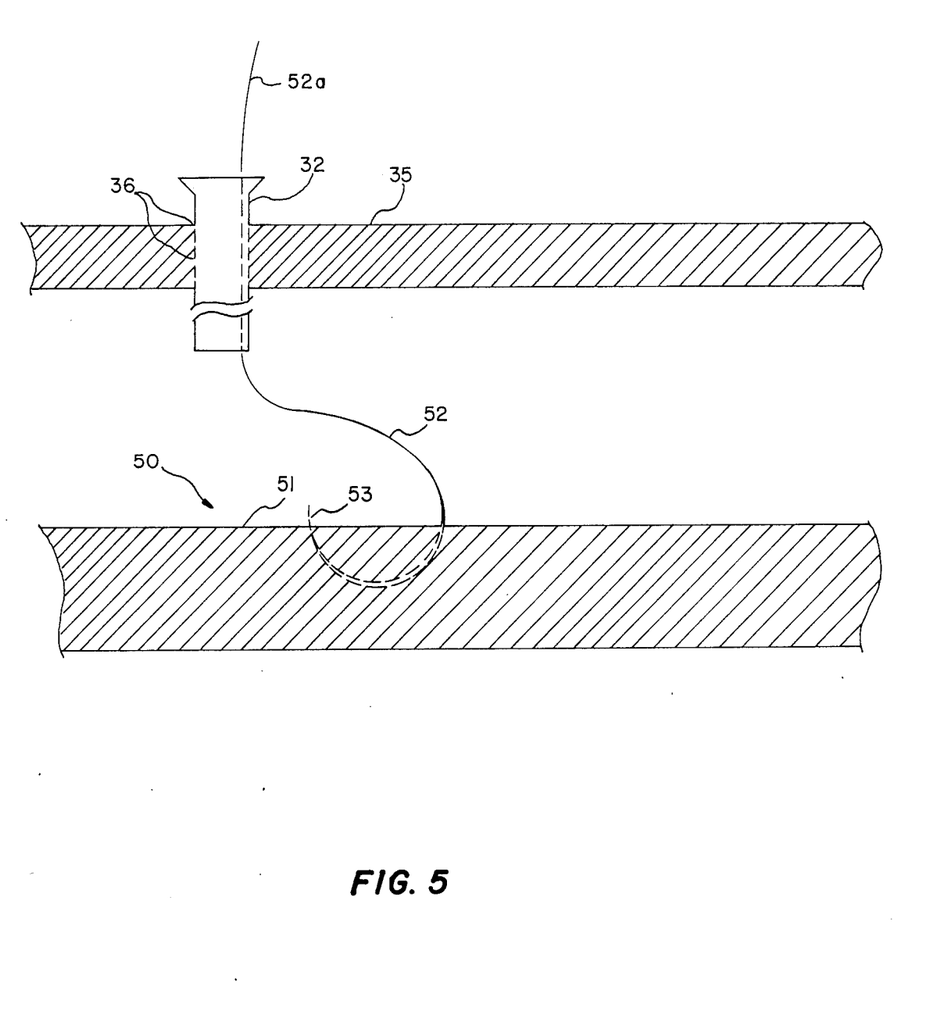
FIGS. 5 through 8 depict the various steps used to attach the device of this invention to an internal wound, the device of this invention being shown in FIGS. 6-8 in cross section for clarity.
Figure 10:
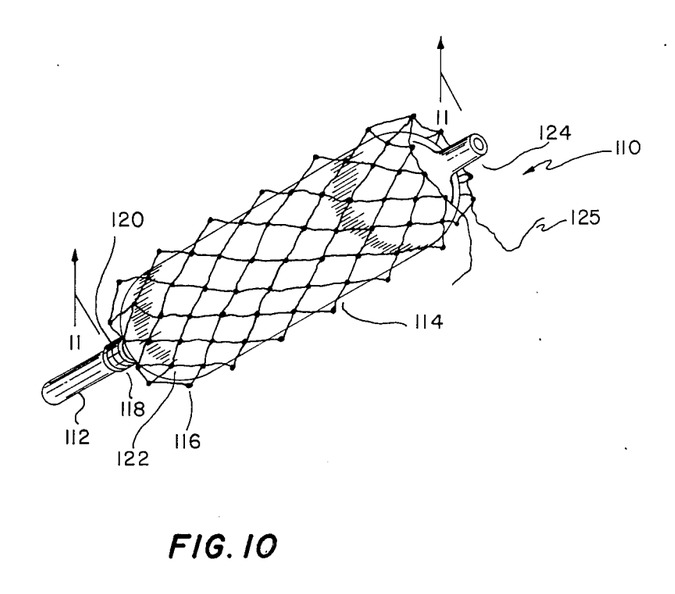
FIG. 10 is a perspective view of an alternative embodiment of this invention.
Figure 11:
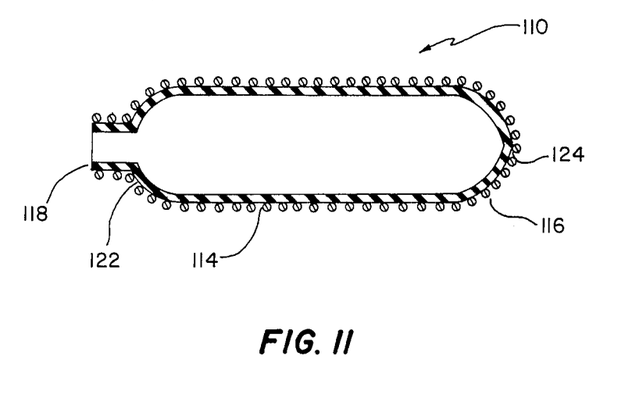
FIG. 11 is a sectional view taken at line 11—11 of FIG. 10.

As best seen in FIG. 3, device 10 is utilized in conjunction with a source of hydraulic pressure such as a bag of fluid 28. Alternatively, air pressure may be used. A connector 30 attaches the hemostatic pressure device 10 to tubing 12 which conveys the hydraulic pressure from the fluid pressure source 28 to device 10. As device 10 is designed for stopping blood flow internally, a trochar tube 32 is employed where a portion of the system 10 passes through an incision 36 in the body of the patient (FIG. 5). If desired, a slide clamp 38 may be used on flexible tubing 12 to control hydraulic pressure. With clamp 38 in the open position, fluid 40 will be allowed to pass from the fluid source 28 into hemostatic pressure device 10 as shown in FIG. 4. Variation in the vertical distance between the source of fluid pressure 28 and balloon 14 can be used to control the hydraulic pressure applied to balloon 14. In FIGS. 10 and 11 a first alternative embodiment 110 is shown. Those portions having the same function and relative location as in the preferred embodiment will be given the same reference numbers as in the preferred embodiment, except that the reference numbers are in the "100" series. Rather than closing head 124 of balloon 114 with a metal ferrule 26 (FIG. 2) as in the preferred embodiment, head 124 of balloon 114 is closed by tying net 116 securely around head 124 of balloon 114 with thread 125.

OPERATION

Figure 6:
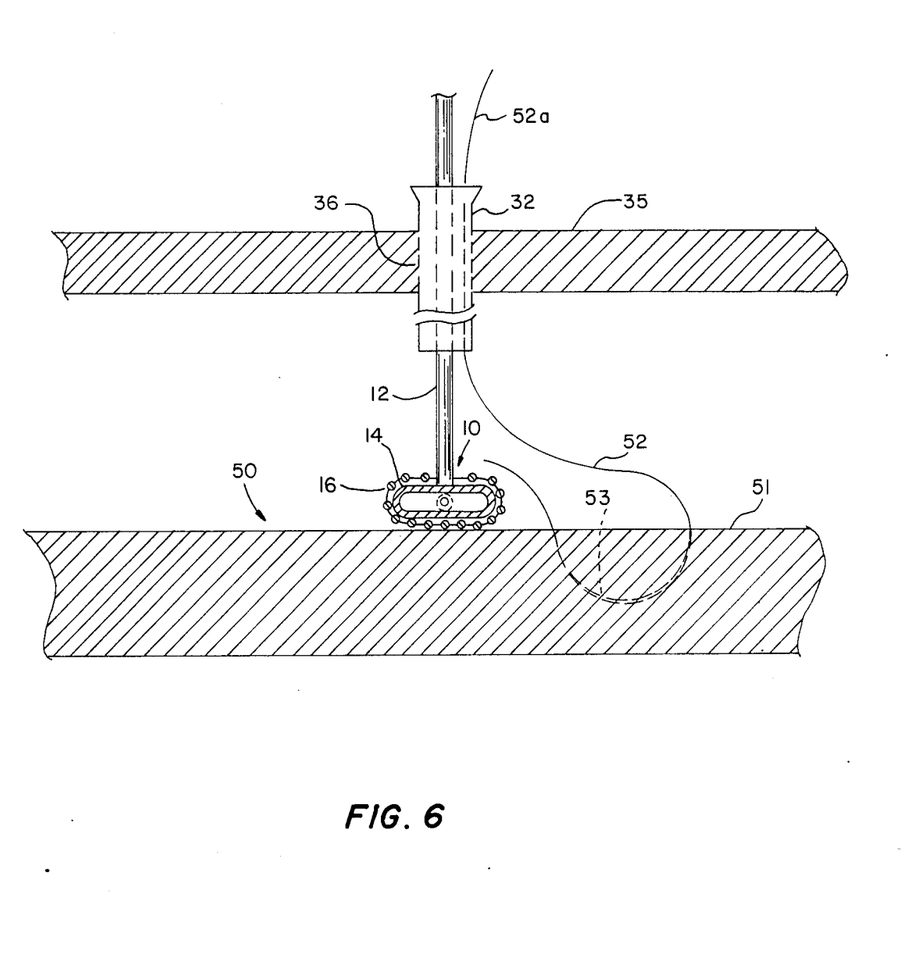
Figure 7:
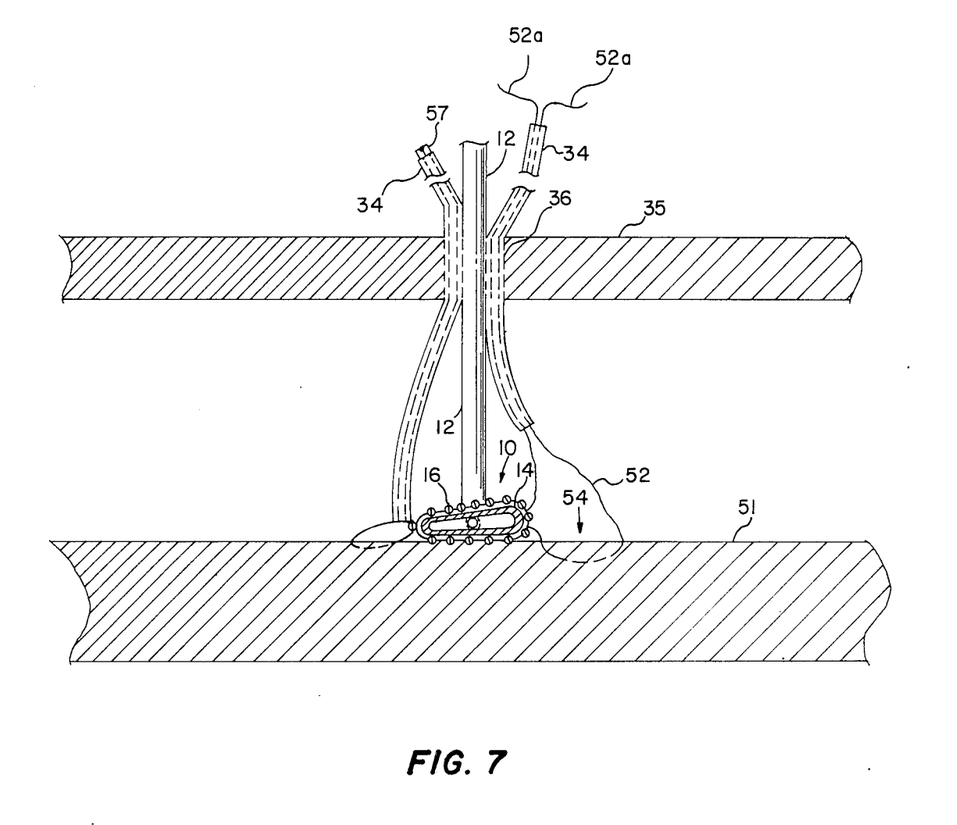
Figure 8:
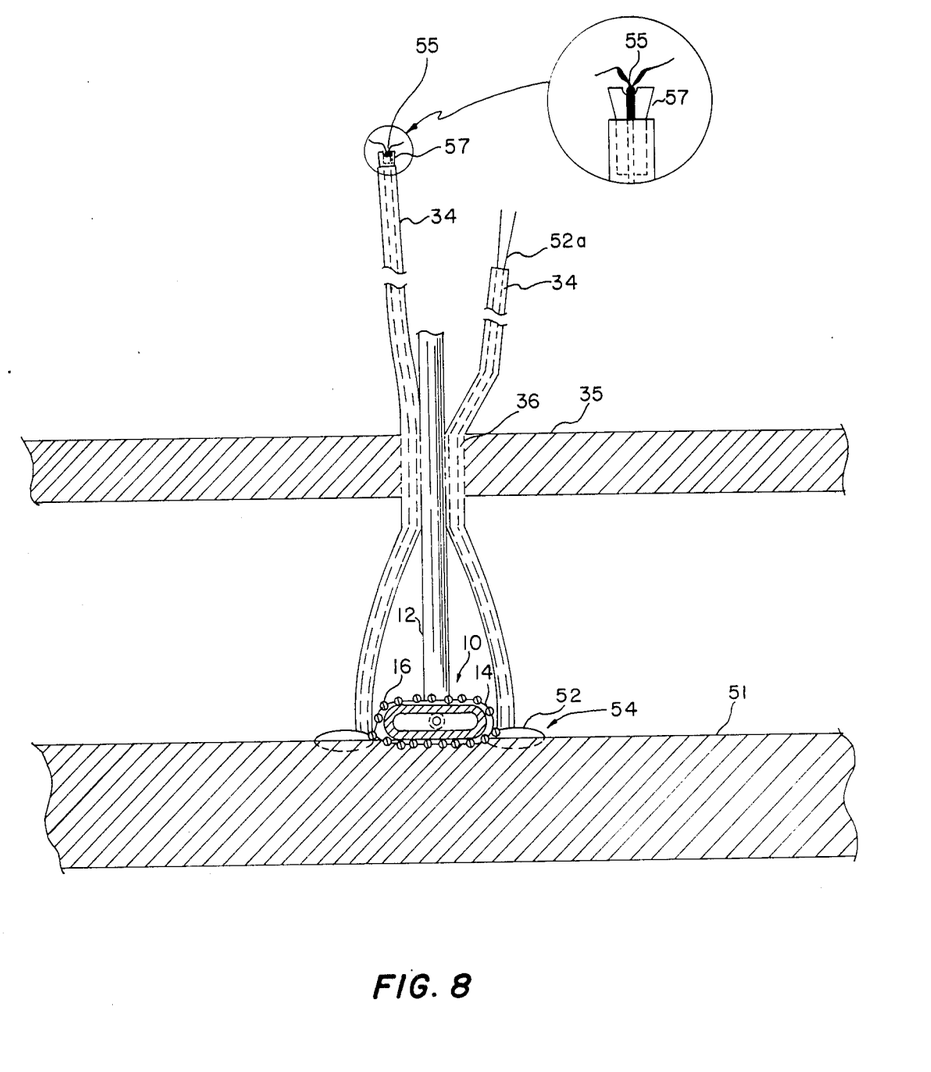
Figure 9:
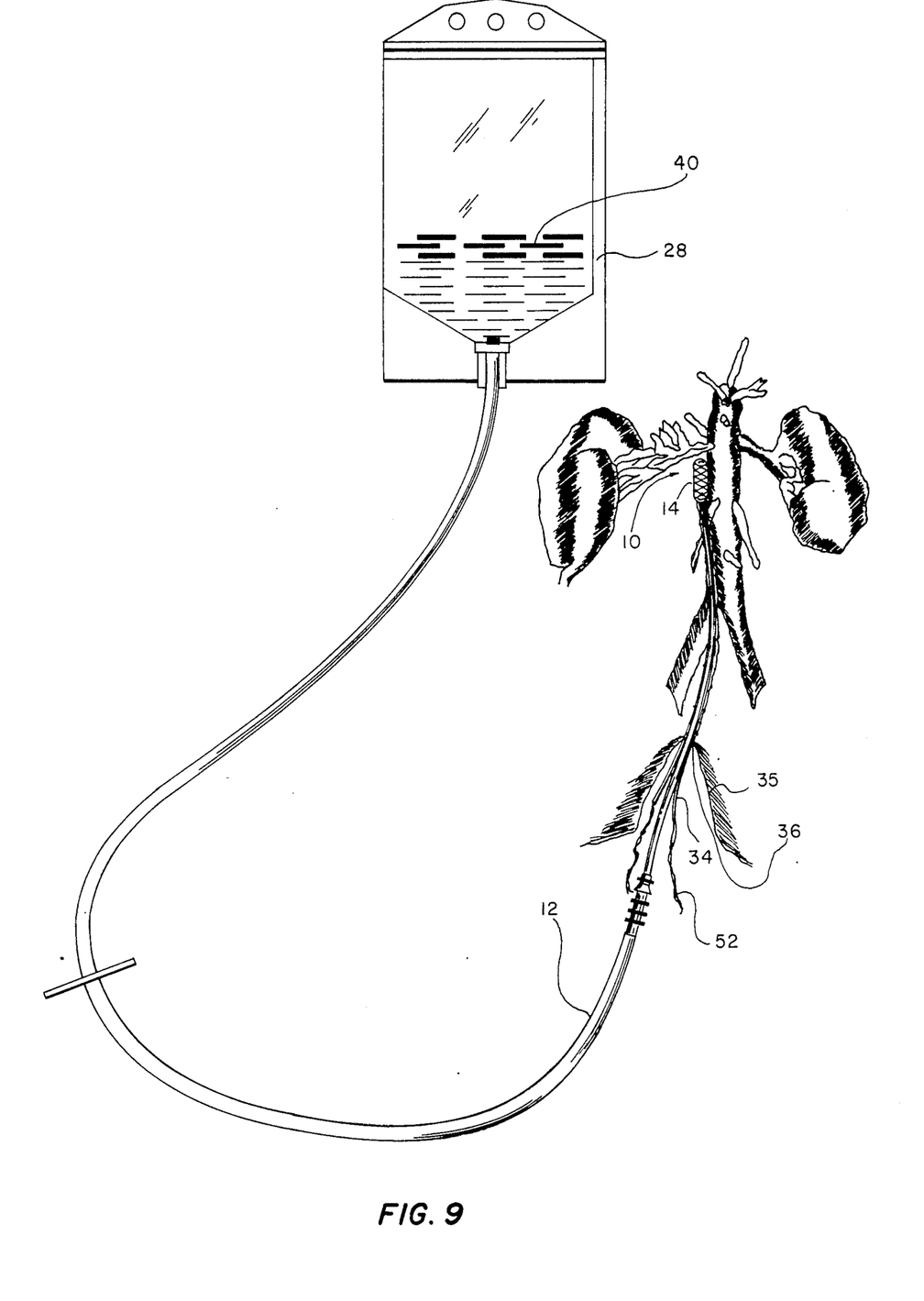
FIG. 9 is a schematic depiction of the device of this invention within the body of a patient once the steps depicted in FIGS. 5 through 8 have been completed.

When a bleeding wound is encountered on an internal portion generally 50 of the body, the hemostatic pressure device 10 of this invention is secured over the bleeding wound as shown in FIGS. 5 through 8. Surgical thread 52 is first conducted through tissue 51 surrounding the bleeding area by a needle 53. Hydrostatic pressure device 10 is then positioned on tissue 51 as shown in FIG. 6. Then as shown in FIG. 7, thread 52 is passed through a portion of net 16 to form sutures generally 54 which hold the net 16 to the area surrounding the bleeding, wound in tissue 51. The ends 52a of thread 52 are conducted from the sutures 54 which surround the wound out through a trochar tube 32 which is inserted through an incision 36 in the skin 35 of a patient as shown in FIGS. 5 and 6. Once sutures 54 are in place, thread 52 is conducted through flexible catheter tubes 34 as shown in FIGS. 7 and 8. Trochar tube 32 is removed and tension is placed on threads 52 by tying a knot 55 in the free end 52a of thread 52 after free ends 52a of thread 52 have been passed through a small stopper 57 which is selected to fit in the end of catheter tubes 34. While a stopper is shown as part of the preferred embodiment, it will be understood that any suitable method of securing ends 52a and 52b of thread 52 at the end of catheter 34 may be employed. Hydraulic pressure is then conveyed to hemostatic pressure device 10 through tube 12. When sutured in place and attached to a source of hydraulic pressure 28 balloon 14 will expand as shown in FIG. 9. Initially, the hydraulic pressure within balloon 14 causes balloon 14 to move away from the wound, but as it expands to fill net 16, the attachment of net 16 to the area surrounding the wound and the filling of net 16 by balloon 14 restrains the movement of balloon 14 away from the wound and thereby increases the direct pressure applied by balloon 14 to the bleeding internal wound. The pressure of balloon 14 directly to the site of bleeding stops the flow of blood from the internal wound. After operative procedures have been completed, hemostatic pressure device 10 may remain in place with pressure supply tubing 12 and catheter tubes 34 passing out of incision 36. When it has been determined that hemostatic pressure device 10 may be removed, fluid 40 is drained from hemostatic pressure device 10 by lowering the source of fluid 28 below hemostatic pressure device 10. This draining of fluid 40 causes balloon 14 to return to its unexpanded state. Loop sutures 54 which attach net 16 to the area surrounding the wound are released by cutting thread 52 and withdrawing thread 52 through catheter tubes 34. Deflated balloon 14 may now be withdrawn through incision 36 which heretofore accommodated pressure tubing 12 and catheter tubes 34.

Device 10 of this invention is typically made from medical grade materials. Specifically, balloon 14 is made from rubber. However, a suitable medical grade plastic may be used. Net 16 is formed of surgical thread. Tubing 12 is typically medical grade flexible plastic tubing.

There is now provided a device which can be used to apply direct pressure to a bleeding wound within the body of a patient. The device can be easily removed when the internal bleeding has stopped. It is apparent that modifications and/or alterations may be made in the form, construction and arrangement of the disclosed hydrostatic pressure device by those having ordinary skill in the art without departing from the spirit and scope of this invention.

I claim:

1. A device for applying hydrostatic pressure to an internal wound comprising:
    an expansible balloon constructed and arranged to hold fluid;

means to restrain the movement of said expansible balloon; and means to conduct fluid to said expansible balloon;

whereby when said expansible balloon is restrained from movement with respect to the wound, fluid may be conducted into said expansible balloon so as to expand said expansible balloon within said means to restrain the movement of said expansible balloon thus applying pressure to the internal wound.

2. The device as defined in claim 1 wherein said means to restrain the movement of said expansible balloon includes a net.

3. The device as defined in claim 2 further including sutures for attaching said net to the area surrounding the wound.

4. A hydrostatic pressure application system for an internal wound comprising:

a source of fluid for applying varying hydraulic pressure;

a balloon constructed and arranged to hold fluid;

means to restrain the movement of said balloon, said means to restrain the movement of said balloon surrounding said balloon; and means to conduct fluid from said source of fluid to said balloon;

whereby when said balloon is restrained from movement away from the internal wound, fluid may be conducted into said balloon from said source of fluid at varying hydraulic pressure so as to expand said balloon and apply pressure to the internal wound.

5. The system as defined in claim 4 wherein said balloon, said means to restrain the movement of said balloon and said means to conduct fluid are constructed and arranged to pass through an incision in their unexpanded state.

6. A hydrostatic pressure application system for an internal wound comprising:

a source of fluid for applying varying hydraulic pressure;

a balloon constructed and arranged to hold said fluid;

a net surrounding said balloon;

a flexible tube for conducting fluid from said source of fluid to said balloon;

surgical thread for attaching said net to the area surrounding the internal wound;

whereby when said balloon is restrained from movement away from the internal wound by said surgical thread, fluid may be conducted into said balloon from said source of fluid at varying hydraulic pressures so as to expand said balloon and apply pressure to the internal wound, but when said balloon is in its unexpanded state, said attachment of said net by said surgical thread may be released, and said balloon, said net and said flexible tube may be removed from the internal site of the wound through an incision in the body.

7. The system as defined in claim 6 wherein that portion of said surgical thread which passes through said incision is shielded by a catheter tube.

8. A method for stopping bleeding from an internal wound comprising the steps of:

attaching an expansible flexible container to a source of hydraulic pressure;

inserting said expansible flexible container into a bag made from an open weave fabric;

securing said bag to the area surrounding the internal wound; and applying hydraulic pressure to the expansible flexible container.

9. The method as defined in claim 8 wherein said bag is secured to the area surrounding the internal wound by sutures of surgical thread.

10. The method as defined in claim 9 wherein said surgical thread is conducted through catheter tubes.

* * * * *